US012745917B2

(12) United States Patent
Poleschner et al.

(10) Patent No.: US 12,745,917 B2
(45) Date of Patent: Sep. 29, 2026

(54) APPARATUS FOR DETERMINING AN INDICATOR REPRESENTATIVE FOR A FLUID RESPONSIVENESS PARAMETER

(71) Applicant: KONINKLIJKE PHILIPS N.V., Eindhoven (NL)

(72) Inventors: Thomas Poleschner, Böblingen (DE); Benjamin Stolze, Taufkirchen (DE); Stephan Guido Maria Regh, Boeblingen (DE); Manuela Braun, Boeblingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 326 days.

(21) Appl. No.: 18/039,580

(22) PCT Filed: Nov. 29, 2021

(86) PCT No.: PCT/EP2021/083267
§ 371 (c)(1),
(2) Date: May 31, 2023

(87) PCT Pub. No.: WO2022/117471
PCT Pub. Date: Jun. 9, 2022

(65) Prior Publication Data

US 2024/0090781 A1 Mar. 21, 2024

(30) Foreign Application Priority Data

Dec. 2, 2020 (EP) .................................... 20211323

(51) Int. Cl.
*A61B 5/022* (2006.01)
*A61B 5/00* (2006.01)
(Continued)

(52) U.S. Cl.
CPC ...... *A61B 5/02225* (2013.01); *A61B 5/02028* (2013.01); *A61B 5/02108* (2013.01); *A61B 5/7246* (2013.01); *A61B 5/725* (2013.01)

(58) Field of Classification Search
CPC ........... A61B 5/02225; A61B 5/02028; A61B 5/02108; A61B 5/7246; A61B 5/725; A61B 5/0205
See application file for complete search history.

(56) References Cited

U.S. PATENT DOCUMENTS 5,577,508 A 11/1996 Medero
5,704,362 A 1/1998 Hersh
(Continued)

FOREIGN PATENT DOCUMENTS

CN 105342590 A 2/2016
EP 2759257 B1 9/2016
WO 2014121945 A1 8/2014

OTHER PUBLICATIONS

International Search Report Dated Feb. 23, 2022 For International Appln. No. PCT/EP2021/083267 Filed Nov. 29, 2021.
(Continued)

*Primary Examiner* — Justin Xu
(74) *Attorney, Agent, or Firm* — Brynne J. Corcoran

(57) ABSTRACT

The invention relates to an apparatus for determining an indicator that is representative of a fluid responsiveness parameter. The indicator is determined based on a fitting of a functional prototype to data values (s0) determined from pulse signals measured over subsequent respiratory cycles. The fitting process is accelerated by a) reducing the number of data values before fitting, b) determining an initial fit parameter value for the functional prototype based on characteristics of the data values and/or a fit parameter value known from a previous fitting, and/or c) carrying out the fitting in several stages, wherein the number of data values
(Continued)

used is increased from stage to stage and a fit parameter value determined in a previous stage is used as initial fit parameter value in a current stage. This allows for a faster determination of the fluid responsiveness parameter.

14 Claims, 13 Drawing Sheets

(51) Int. Cl.

| | |
|---|---|
| ***A61B 5/02*** | (2006.01) |
| ***A61B 5/0205*** | (2006.01) |
| ***A61B 5/021*** | (2006.01) |

(56) References Cited

U.S. PATENT DOCUMENTS

| | | | | |
|---|---|---|---|---|
| 11,857,302 | B2 | 1/2024 | Knoll | |
| 2013/0030262 | A1* | 1/2013 | Burnett | A61M 25/0017 600/484 |
| 2018/0317808 | A1 | 11/2018 | Wang | |
| 2019/0336015 | A1* | 11/2019 | Knoll | A61B 5/0295 |
| 2023/0046598 | A1* | 2/2023 | Cohen | G16B 5/30 |

OTHER PUBLICATIONS

P.K. Lim et al. "Improved Measurement of Blood Pressure by Extraction of Characteristic Features from the Cuff Oscillometric Waveform", SENSORS, vol. 15, pp. 14142 to 14161 Jun. 16, 2015.

* cited by examiner

APPARATUS FOR DETERMINING AN INDICATOR REPRESENTATIVE FOR A FLUID RESPONSIVENESS PARAMETER

CROSS-REFERENCE TO PRIOR APPLICATIONS

This application is the U.S. National Phase application under 35 U.S.C. § 371 of International Application No. PCT/EP2021/083267, filed on Nov. 29, 2021, which claims the benefit of European Application No. 20211323.9 filed on Dec. 2, 2020. These applications are hereby incorporated by reference herein.

FIELD OF THE INVENTION

The invention relates to an apparatus, a method and a computer program for determining an indicator that is representative for a fluid responsiveness parameter.

BACKGROUND OF THE INVENTION

U.S. Pat. No. 5,704,362 A discloses a method for measuring blood pressure of a subject. A plurality of oscillometric data values is obtained from a complex amplitude taken at a plurality of pressure levels. A function curve having a physiologically-expected shape of an oscillometric envelope is selected, wherein the function curve is defined by a parameter. The function curve is fitted to the plurality of data values by computing the parameter of the function curve such that an error between the function curve and the data values is minimized at the plurality of pressure levels, wherein finally a systolic blood pressure and a diastolic blood pressure are computed based on the fitted function curve.

U.S. Pat. No. 5,577,508 A1 discloses an automated sphygmomanometer apparatus with an inflatable and deflatable pressure cuff and inflating means operatively coupled to the cuff for selectively applying a medium under a pressure to the cuff for inflating and pressurizing the cuff. The cuff further comprises cuff pressure sensing means coupled to the cuff for sensing cuff pressure including arterial blood pressure oscillations therein. The apparatus also comprises deflating means operatively coupled to the cuff for selectively relieving pressure from the cuff. Control means control the inflating means to inflate the cuff and the deflating means to deflate the cuff to respective cuff pressure levels for the detection of the arterial blood pressure oscillations at each of the cuff pressure levels during a blood pressure determination. An oscillometric envelope is determined, which comprises pulse amplitude points corresponding to the arterial blood pressure oscillations at the respective cuff pressure levels during the blood pressure determination. The oscillometric envelope is linearly approximated with a pair of best fit lines, wherein a mean arterial pressure of the patient is determined based on a pressure at a point of intersection of the pair of best fit lines.

The article "Improved Measurement of Blood Pressure by Extraction of Characteristic Features from the Cuff Oscillometric Waveform" by P. K. Lim et al., SENSORS, volume 15, pages 14142 to 14161 (2015) discloses a method for determining systolic and diastolic blood pressure from oscillometric waveform data, and CN 105342590 A discloses an oscillometric method for measuring blood pressure.

EP 2 759 257 B1 discloses a method for determining an indicator that is representative for a patient's volume responsiveness. A sequence of pulse signals of a patient over a time period corresponding to a plurality of subsequent respiratory cycles of the patient is measured, wherein the sequence of measured pulse signals is detected by a non-invasive pulse measurement method using a pressure cuff, wherein the pressure applied in the pressure cuff is continuously increased or decreased in the course of a measurement period. The measured pulse signals are represented as pulse signals oscillating around an average value thereof, wherein an envelope signal curve for the pulse signals is determined. Moreover, a fit envelope signal function is determined based on the previously determined envelope signal curve, wherein the fit envelope signal function is determined based on a predetermined first functional prototype and represents an idealized curve progression of the envelope signal curve over the plurality of respiratory cycles without comprising pulse variations caused by ventilation or respiration induced heart-lung interaction. Then, respiratory pulse variation signals are determined, which correspond to the pulse variations caused by ventilation or respiration induced heart-lung interaction over the plurality of respiratory cycles, wherein the determined respiratory pulse variation signals correspond to a difference between the envelope signal curve and the fit envelope signal function. As a next step, an envelope respiration curve is determined for the previously determined respiratory pulse variation signals and a fit envelope respiration function is determined based on the previously determined envelope respiration curve, wherein the fit envelope respiration function is determined based on a predetermined second functional prototype and represents an idealized curve progression of the envelope respiration curve over the plurality of respiratory cycles. Finally, the indicator that is representative for the patient's volume responsiveness is determined based on the fit envelope signal function and the fit envelope respiration function.

The fit envelope signal function is determined by fitting a Cauchy-Lorentz function to the envelope signal function by using a Levenberg-Marquardt algorithm. Moreover, the fit envelope respiratory function is determined by fitting the Cauchy-Lorentz function to the envelope respiratory function also by using the Levenberg-Marquardt algorithm.

The Levenberg-Marquardt algorithm can be computationally very intensive and hence time consuming such that the time needed for determining the indicator that is representative for the patient's volume responsiveness is generally very long.

SUMMARY OF THE INVENTION

It is an object of the present invention to provide an apparatus, a method and a computer program which allow for a faster determination of an indicator that is representative for a fluid responsiveness parameter.

In a first aspect of the present invention an apparatus for determining an indicator that is representative for a fluid responsiveness parameter is presented, wherein the apparatus comprises:

a pulse signals providing unit configured to provide a sequence of measured pulse signals of a patient over a time period corresponding to a plurality of subsequent respiratory cycles of the patient, wherein the sequence of measured pulse signals has been detected by a non-invasive pulse measurement method, an indicator determination unit configured to carry out a determination procedure adapted to determine an indicator that is representative for a fluid responsiveness parameter based on the provided sequence of pulse signals, wherein the determination procedure includes a determination of data values based on the provided sequence of pulse signals and a fitting of a provided functional prototype, which depends on a fit parameter to be modified during the fitting, to the determined data values, wherein the indicator determination unit is configured such that a), before the fitting, the number of data values is reduced for the entire fitting, and/or b) an initial value is determined for the fit parameter based on characteristics of the data values which are related to characteristics of the functional prototype and/or based on a value of the fit parameter known from a previous fitting, and/or c) the fitting is carried out in several stages, wherein the number of data values used for the fitting is increased from stage to stage and wherein in a current stage a value of a fit parameter determined in a previous stage is used as initial value for the fit parameter in the current stage.

Reducing, before the fitting, the number of data values for the entire fitting, determining an initial value for the fit parameter based on characteristics of the data values which are related to characteristics of the functional prototype and/or based on a value of the fit parameter known from a previous fitting, and carrying out the fitting in several stages, wherein the number of data values used for the fitting is increased from stage to stage and wherein in a current stage a value of a fit parameter determined in a previous stage is used as initial value for the fit parameter in the current stage, significantly reduces the calculation time. This allows for a faster determination of the indicator that is representative for the fluid responsiveness parameter.

The fluid responsiveness parameter is preferentially a fluid responsiveness parameter of a patient. It also could be a fluid responsiveness parameter of a volunteer or an animal. The fluid responsiveness parameter is indicative of, or corresponds to, a patient's volume or fluid responsiveness, i.e. the fluid responsiveness could also be called "volume responsiveness". Accordingly, the determination of the indicator that is representative for the fluid responsiveness parameter is preferentially a determination of the fluid responsiveness parameter (FRP), especially of a pulse pressure variation (PPV), a systolic pressure variation (SPV) and/or a stroke volume variation (SVV). In these particular cases, the determined indicator may be the respective FRP, i.e. a PPV, an SPV and/or an SVV.

The provision of the sequence of measured pulse signals can correspond to measuring the sequence of pulse signals of the patient, particularly to measuring signals corresponding to blood pulsations by continuously or semi-continuously recording a pressure indicative of the blood pulsations. In an embodiment the sequence of measured pulse signals has been detected by a non-invasive pulse measurement method using a pressure cuff, wherein the pressure applied in the pressure cuff is continuously increased or decreased in the course of a measurement period. The measured signals might then correspond to continuous or semi-continuous recordings of a pressure in the pressure cuff. The provision of the sequence of measured pulse signals may also comprise a providing of a sequence of pulse signals which have been measured previously by, for instance, a physician. The measured pulse signals may hereafter have been stored and this stored sequence might be provided. Generally, non-invasive pulse measurements methods include, for instance, oscillometric methods. In oscillometric pulse measurement methods, usually a pressure cuff is inflated such that a pneumatic coupling between blood pulsations and a pressure sensor recording a pressure in the inflated volume is generated. Preferably, however, the sequence of pulse signals is measured using a pressure cuff that is adapted to provide a hydraulic coupling between blood pulsations and a pressure sensor of the pressure cuff that is adapted to record the pressure indicative of the blood pulsations. A pressure cuff of this kind is disclosed, for instance, in WO 2014/121945 A1. Using such a pressure cuff, which will subsequently be referred to also as a high-fidelity pressure cuff, allows for an improved quality of the recorded pressure signal as compared to oscillometric measurements relying on a pneumatic coupling. For instance, the pressure cuff may be adapted to bring the pressure sensor into direct contact with the patient's tissue such that it is hydraulically coupled to blood pulsations via the tissue, wherein preferentially there is no air between the pressure sensor and the patient's tissue, i.e. the patient's skin, in order to ensure the hydraulic coupling between the blood in the vessel and the pressure sensor. The pressure cuff may, for instance, be a high-fidelity upper arm pressure cuff. The hydraulic coupling of the pressure sensor to the blood pulsations allows for a more accurate detection of the blood pulsations and hence for an improved determination of the fluid responsiveness parameter based on the measured pulse signals.

The pressure cuff can comprise a fluid based pressure sensor including, besides a pressure sensing element performing the actual pressure measurement like a pressure transducer, for instance a fluid filled sensor pad on the patient's skin connected to the pressure sensing element. The sensor pad can be filled with a water-based gel, silicone oil or another fluid. The pressure sensing element can be located within or on the sensor pad, or it can be located with a distance to the sensor pad, wherein in this case a fluid is used for providing a hydraulic coupling between the sensor pad and the pressure sensing element by means of, for instance, a tube filled with the fluid and extending between the sensor pad and the pressure sensing element. Instead of the fluid filled sensor pad also another fluid filled element can be used like a fluid filled pressure sensitive film. Also if the pressure cuff uses a fluid based pressure sensor with the pressure sensing element, the pressure sensor preferentially is airlessly coupled to the outer skin. Moreover, preferentially the fluid is an incompressible fluid. Thus, in an embodiment, the pressure cuff comprises a fluid based pressure sensor with an incompressible fluid filled pressure sensitive film or fluid filled sensor pad coupled airlessly to tissue, i.e. to the outer skin, wherein a limb is partially or fully surrounded.

The determination procedure that the indicator determination unit is adapted to carry out includes a determination of data values based on the provided sequence of measured pulse signals. For instance, the pulse signals providing unit may be configured to provide the sequence of measured pulse signals as a continuous or a quasi-continuous digital signal, wherein the indicator determination unit may be adapted to determine the data values by discretizing the provided sequence of measured pulse signals and/or determining a start and an end point of the provided sequence of measure pulse signals. The data values may then still be understood as a direct representation, or sampling, of the sequence of measured pulse signals. Determining the data values based on the provided sequence of measured pulse signals may, however, additionally or alternatively also comprise other types of preprocessing of the measured pulse signals, such as, for instance, the determination of an envelope signal curve, of respiratory pulse variation signals and/or of a signal or curve derived from the respiratory pulse variation signals, such as an absolute respiratory pulse variation curve, like an envelope respiration curve or a another curve indicative of absolute values of the respiratory pulse variation signals, for the measured pulse signals. The data values may then correspond to the envelope signal curve or the signal or curve derived from the respiratory pulse variation signals, respectively, i.e., for instance, to a discretized version of it.

The determination procedure further includes a fitting of a predetermined functional prototype to the determined data values. The functional prototype can depend on one or more fit parameters to be modified during fitting, wherein an initial value for each of the one or more fit parameters can be determined. The initial value for each or only some of the one or more fit parameters can be determined based on characteristics of the data values which are related to characteristics of the functional prototype and/or based on a value of the respective fit parameter known from a previous fitting. For those of the one or more fit parameters whose initial values are not determined based on characteristics of the data values which are related to characteristics of the functional prototype and/or based on a value of the respective fit parameter known from a previous fitting, the initial value might be predefined or determined based on characteristics of the measurement method, such as rate of change in pressure applied in a pressure cuff, for instance.

The functional prototype can be predetermined depending on an expected form of the sequence of measured pulse signals, wherein the form might be expected, for instance, based on the measurement method. Moreover, the functional prototype can also be predetermined depending on a chosen manner of determining the data values based on the provided sequence of measured pulse signals, wherein the chosen manner may correspond, for instance, to a defined preprocessing.

In an embodiment the pulse signals providing unit is configured to provide several sequences of measured pulse signals of a patient over time, wherein each of the sequences of measured pulse signals has been detected in a different time period and wherein the indicator determination unit is configured to determine a set of data values for each of the provided sequences of measured pulse signals. The different time periods may, for instance, correspond to subsequent cycles of inflation and/or deflation of the pressure cuff.

For fitting the provided functional prototype to the determined data values, any known fitting algorithm may be used. Preferentially, a non-linear least squares algorithm may be used, particularly the Levenberg-Marquardt algorithm. It is understood, however, that the above indicated effect of reduced computational efforts can also be achieved for different fitting algorithms.

In an embodiment the indicator determination unit is configured to reduce the number of data values such that the reduced number of data values fulfills the Shannon-Nyquist criterion with reference to a bandwidth of the provided functional prototype and/or with reference to the data values themselves. For instance, the number of data values may be reduced such that the reduced number of data values fulfills the Shannon-Nyquist criterion with reference to the provided sequence of pulse signals based on which the data values have been determined. This may particularly be the case if the data values are determined such that they are representative of the provided sequence of pulse signals. The bandwidth of the provided functional prototype, particularly the frequencies contained therein, may, for instance, be estimated based on a time elapsed during the increase or decrease in pressure in the pressure cuff from a first pressure value to a second pressure value, wherein the first pressure value and the second pressure value may refer, for instance, to a diastolic and a systolic arterial pressure value, respectively. If the data values are determined such that they are representative of the respiratory cycles of the patient, the number of data values may be reduced such that the reduced number of data values fulfills the Shannon-Nyquist criterion with reference to the respiratory cycles of the patient. For example, when data values having samples every 0.004 s and a maximum frequency of interest of 0.5 Hz are fitted to a bell-shaped curve with a full width at half maximum of 20 . . . 100 s, a reduction of data values to be fitted can be done by selecting one data value per second.

In an embodiment the indicator determination unit is configured to reduce the number of data values by determining one data value at a predetermined frequency and/or by downsampling. In a further embodiment the indicator determination unit is configured to lowpass filter the data values before reducing the number of data values.

It is preferred that the functional prototype is a bell-shaped function. This is particularly preferred if the sequence of measured pulse signals has been detected using a pressure cuff, wherein the pressure applied in the pressure cuff is continuously increased or decreased in the course of a measurement period. The bell-shaped function is preferentially a Cauchy-Lorentz function. The bell-shaped function can have a first fit parameter being indicative of the height of the maximum of the bell-shaped function and a second fit parameter being indicative of the position of the maximum of the bell-shaped function, wherein the indicator determination unit can be configured to determine a height of a maximum of the data values and a position of the maximum of the data values as initial values for the first and second fit parameters.

Providing initial values for the fit parameters, which are close to the final values for the fit parameters, can reduce calculation time significantly. This prediction can be done by analyzing the data values for characteristics that describe the functional prototype. Predetermination and preselection of characteristic patterns from the data values can make the data values fit better to the functional prototype and thereby reduce the total number of iterations during fitting. For example, by fitting, as explained above, to a bell-shaped functional prototype, in which at least two of the fit parameters are the height and position of the maximum, the height and position of the maximum of the data values can be used as initial values for the fit parameters. A third fit parameter on which the bell-shaped functional prototype can depend might relate to the full width at half maximum. An initial value for this third fit parameter can be determined without reference to the data values, namely a) based on the time elapsed during an increase in pressure in the pressure cuff from a first pressure value to a second pressure value or a decrease in pressure in the pressure cuff from the second pressure value to the first pressure value, wherein the first pressure value and the second pressure value may refer, for instance, to a diastolic and a systolic arterial pressure value, respectively, or b) directly as the width of a pressure range including the first and the second pressure value, wherein the pressure range may be, for instance, a range from 0.7 times the diastolic arterial pressure value to 1.3 times the systolic arterial pressure value or a range from 10 mmHg below the diastolic arterial pressure value to 20 mmHg above the systolic arterial pressure value. The diastolic and systolic arterial pressure values that may be used for determining the third fit parameter may refer, for instance, to predefined standard or known average values, or to values previously measured for the patient.

In an embodiment the indicator determination unit is configured such that the fitting is carried out in three stages, wherein in a first stage a first percentage of the data values, in a following second stage a higher, second percentage of the data values and in a following third stage 100 percent of the data values are used. For instance, the first percentage can be 1/10 percent and the second percentage 1 percent. The first percentage and second percentage can also be, for instance, percentages corresponding to 1/250 and $\sqrt{1/250}$, i.e. 0.4 percent and approximately 6.32 percent, respectively.

It is possible that, when applying this multiple staged fitting, the total number of iterations is larger than simply applying the fit algorithm on the originally determined data values. However, overall calculation time is generally shorter, because most or all of the stages are done on a reduced amount of data values to be calculated with.

In a preferred embodiment the indicator determination unit is configured such that the fitting is carried out in several stages, wherein, after the fitting has been carried out in a stage, it is determined whether the fitted fit parameter is in conformance with an abort criterion, wherein, if this is the case, the fitting is terminated.

For instance, the indicator determination unit can be configured to use a deviation between a) a fitted value of the fit parameter, which resulted from a respective stage, and b) an expected value of the fit parameter as the abort criterion. In cases in which the fit algorithm is not yielding valid data, for instance, because the underlying data values are not forming a shape related to the functional prototype, analyzing the fit results of each stage before the final stage on validity can lead to the conclusion that not all stages have to be executed, thereby avoiding unnecessary calculation effort and therefore reducing runtime. This can be done, as explained above, when there is a certain range of expected values of the final fit parameters and the stages before the final stage yield fit parameters too far off these ranges.

It is also possible that the abort criterion indicates that the fit parameters resulting from a stage are already very well, for instance, by determining whether a deviation between fit parameters resulting from a current stage from fit parameters resulting from a previous stage is smaller than a predefined threshold, wherein in this case the fitting can be stopped, before the final stage has been carried out. Also this allows for a reduced calculation time.

When fitting is carried out in several stages, i.e. in the case of multiple-staged fitting, and if the original number of data values is used for the fitting in the last stage, the final results, particularly the accuracy of the final determined fit parameters, can be the same as compared to a single-staged fitting to the original number of data values, even though the overall calculation time can be reduced. To allow for a further reduction in overall calculation time, fitting may also be carried out in several stages such that even for the fitting in the final stage less than the original number of data values is used.

In a preferred embodiment the pulse signals providing unit is configured to represent the measured pulse signals as pulse signals oscillating around an average value thereof and the indicator determination unit is configured such that first data values are determined by determining an envelope signal curve for the pulse signals, in a first fitting, a provided first functional prototype, which depends on a first fit parameter to be modified during the first fitting, is fitted to the first data values such that a resulting fit envelope signal function represents an idealized curve progression of the envelope signal curve over the plurality of respiratory cycles without comprising pulse variations caused by ventilation or respiration induced heart-lung interaction, respiratory pulse variation signals corresponding to the pulse variations caused by ventilation or respiration induced heart-lung interaction over the plurality of respiratory cycles are determined, wherein the determined respiratory pulse variation signals correspond to a difference between the envelope signal curve and the fit envelope signal function, second data values are determined by determining an absolute respiratory pulse variation curve for the respiratory pulse variation signals, in a second fitting, a provided second functional prototype, which depends on a second fit parameter to be modified during the second fitting, is fitted to the second data values such that a resulting fit respiration function is indicative of an idealized progression in amplitude of the absolute respiratory pulse variation curve over the plurality of respiratory cycles, and the indicator that is representative for the fluid responsiveness parameter is determined based on the fit envelope signal function and the fit respiration function, wherein a), before the first fitting, the number of first data values is reduced for the entire first fitting, and/or b) an initial value is determined for the first fit parameter based on characteristics of the first data values which are related to characteristics of the first functional prototype and/or based on a value of the first fit parameter known from a previous first fitting, and/or c) the first fitting is carried out in several stages, wherein the number of first data values used for the first fitting is increased from stage to stage and wherein in a current stage a value of the first fit parameter determined in a previous stage is used as initial value for the first fit parameter in the current stage, and/or wherein a), before the second fitting, the number of second data values is reduced for the entire second fitting, and/or b) an initial value is determined for the second fit parameter based on characteristics of the second data values which are related to characteristics of the second functional prototype and/or based on a value of the second fit parameter known from a previous second fitting, and/or c) the second fitting is carried out in several stages, wherein the number of second data values used for the second fitting is increased from stage to stage and wherein in a current stage a value of the second fit parameter determined in a previous stage is used as initial value for the second fit parameter in the current stage. This is particularly preferred if the sequence of measured pulse signals has been detected using a pressure cuff, wherein the pressure applied in the pressure cuff is continuously increased or decreased in the course of a measurement period.

The sequence of measured pulse signals may be detected over a configurable time period. Preferentially, the time period is configured such that it covers a defined number of subsequent respiratory or ventilation cycles of the patient, wherein the predetermined number may be any number from one to ten. For instance, the time period may be configured to have a length of between, for instance, 10 seconds and four minutes, preferably between 30 seconds and two minutes, more preferably about one minute. The pulse rate of the patient depends on various factors, such as age, stress, et cetera. The heart of an adult beats usually between 50 to 90 times per minute. Thus, a comparatively larger number of pulse variations caused by heartbeats can be detected in the detection time period. Such an approach can be advantageous in view of the data quality underlying the calculation of the indicator representative for the fluid responsiveness parameter. However, when applying a non-invasive pressure measurement method using a high-fidelity pressure cuff, the detection period should preferably not exceed three minutes so as to avoid adverse effects due to disturbed blood flow caused by the pressure of the pressure cuff.

The patient's respiration has a detectable influence on pulse variation. While the measured variation of the pressure is primarily derived from the function of the heart, i.e. from its cyclic contractions and relaxations, there is also another influential factor to be considered: Thus, two functions are superimposed: Variations of higher frequency caused by the function of the heart are superimposed by variations of lower frequency caused by the respiration or ventilation of the patient. Notably, such low frequency variations caused by the patient's respiration are not only detected with mechanically ventilated patients, but also with non-ventilated patients breathing spontaneously. Even though the effect of spontaneous breathing is somehow similar to the effect of mechanical ventilation as to variations of pressure, both effects are actually not the same for the following reason: In the case of mechanical ventilation, air is pressed at high pressure from outside into the lungs during inspiration, whereas, in case of spontaneous breathing, air is sucked by lower pressure into the lungs during inspiration. Irrespective of these phenomenological distinctions, in an embodiment the apparatus can be equally applied to mechanical ventilated and spontaneous breathing non-ventilated patients, provided that the respiration—or ventilation—induced maneuver produces significant heart-lung-interaction.

The measured pulse signals may be represented as a function over time or, alternatively, as a function over a clamping pressure exerted by the pressure cuff, wherein the pressure applied in the pressure cuff is continuously increased or decreased in the course of the measurement period.

The envelope signal curve, to which the first data values may correspond, is determined based on the sequence of measured pulse signals. Usually, an envelope curve or function of a rapidly varying signal is considered to be a smooth curve outlining the extremes in amplitude of the rapidly varying signal. For example, the envelope curve or function may be determined by simply connecting the maxima or the minima of the rapidly varying signal. However, preferentially the envelope curve of the pressure signals, i.e. the envelope signal curve, is determined by continuously determining a distance dimension of the measured pulse signals from an average thereof and, thereafter, preferably by applying a low pass filter to the distance dimension. Preferably, the low pass filter has a cutoff frequency below the pulse rate of the patient. For example, the portion below the average value of the oscillating curve of measured pulse signals is preferably folded up to the upper portion. Then, the resulting curve is preferably flattened by using a low pass filter having a cutoff frequency below the pulse rate of the patient. The resulting curve can be flattened in such a way that the area below the flattened curve remains unchanged as compared to the area under the non-flattened curve. Optionally, the flattened curve may additionally be multiplied by a predetermined value. If the flattened curve is multiplied, for example, by the square root of 2, the finally obtained envelope signal curve substantially is at the level of the upper extremes in amplitude of the measured pulse signals.

The distance dimension could also be defined as the squared signal or the extreme values within a certain region, for instance, of about one pulse width or any other metric function. More generally, the distance dimension could also be defined, for instance, as the absolute value of the difference between the signal and its average value to the power of n, wherein n may be 1 or any other number. In case of using the absolute value of the difference as a distance dimension, the result correlates well with the SVV as well as the PPV. Also with the absolute value of the difference to the power of 2 as a distance dimension, the result correlates well to SVV as well as PPV. Preferably, the absolute value of the difference to the power of 2 is used as the distance dimension if the SVV is to be determined, and the absolute value of the difference is used as the distance dimension if the PPV is to be determined. With raising n, the correlation may be further increased. With the maximum metric, i.e. with infinite n as a distance dimension, the result correlates very well with PPV. For example, the maximum metric could be realized by searching the maximum value minus the minimum value of the difference within a moving window equal to the duration of a heartbeat.

The average value, which may be used as the basis of the distance dimension calculation, of the measured pulse signals can be determined as moving average over a period of one single pulse cycle of the patient. Given a series of numbers, which in this case are the measured pulse signals, and a fixed subset size, which in this case is the period of one single pulse cycle of the patient, the first element of the moving average is obtained by taking the average of the initial fixed subset of the number series. Then the subset is modified by "shifting forward", that is excluding the first number of the series and including the next number following the original subset in the series. This creates a new subset of numbers, which is averaged. This process is repeated over the entire data series.

In some instances, it may be advantageous, in order to obtain a well-fittable envelope signal curve, to apply a window function to the measured pulse signals before determining the envelope signal curve. However, since the pulse signals are measured using a non-invasive pressure measurement method employing a high-fidelity pressure cuff, application of a window function may not be required. Under such circumstances, measured pulse signals usually already exhibit a bell-shaped form, and, therefore, are—as such—well fittable with a functional prototype also exhibiting a bell-shaped form. If a window function is applied, the window function is preferably a non-negative smooth bell-shaped curve, for example a Cauchy-Lorentz function.

The determination of the fit envelope signal function represents an idealized curve progression of the envelope signal curve with the object to exclude any pulse variation caused by ventilation or respiration induced heart-lung interaction.

The difference between the envelope signal curve and the fit envelope signal function reflects a modulation which is due to the respiration or ventilation of the patient. Thus, respiratory pulse variation signals corresponding to the pulse variations caused by the respiration of the patient are determined. Preferably, the respiratory pulse variation signals are determined in such a way that the respiratory pulse variation signals oscillate around an average value thereof. Preferably, the area defined by the lower part of the curve of the respiratory pulse variation signals, i.e. the area below the average value, substantially corresponds to the area defined by the upper part of the curve of the respiratory pulse variation signals, i.e. the area above the average value.

The absolute respiratory pulse variation curve may correspond to an envelope respiration curve, in which case the fit respiration function might also be regarded as a fit envelope respiration function. The fit respiration function may then represent an idealized curve progression of the envelope respiration curve over the plurality of respiratory cycles. The determination of the envelope respiration curve, which might in that case correspond to the second data values, is based on the previously determined respiratory pulse variation signals. Preferably, the envelope respiration curve is calculated by continuously determining a distance dimension of the respiratory pulse variation signals from an average thereof and by thereafter preferably applying a low pass filter to the distance dimension. Preferably, the low pass filter has a cutoff frequency below the respiration frequency of the patient. In other words, the portion below the average value of the oscillating curve of respiratory pulse variation signals is preferably folded up to the upper portion. Then, the resulting curve is preferably flattened by using a low pass filter having a cutoff frequency below the respiration frequency of the patient. The curve can be flattened in such a way that the area below the flattened curve remains unchanged as compared to the area under the non-flattened curve. Optionally, the flattened curve may additionally be multiplied by a predetermined value. If the flattened curve is multiplied, for example, with the value of the square root of 2, the finally obtained envelope respiration curve substantially is at the level of the upper extremes in amplitude of the respiratory pulse variation signals. Preferably, the average value, which is used as the basis of the distance dimension calculation, of the respiratory pulse variation signals is determined as moving average over a period of one single respiration cycle of the patient.

Preferentially, the absolute respiratory pulse variation curve does not correspond to an envelope respiration curve, but to a different curve indicative of absolute values of the respiratory pulse variation signals. That is to say, it may be preferred that the fit respiration function is determined without first determining an envelope respiration curve for the previously determined respiratory pulse variation signals and then determining the fit respiration function based on the envelope respiration curve. Instead, it may be preferred to determine the fit respiration function by fitting the second functional prototype to data values, i.e. second data values, corresponding to a different kind of absolute respiratory pulse variation signals, i.e. to data values derived differently from the respiratory pulse variation signals. Nevertheless, such different kind of preprocessing might involve one or more of the steps described above with respective to the determination of the envelope respiration curve from the respiratory pulse variation signals. In an embodiment the absolute respiratory pulse variation curve, which may correspond to the second data values, is determined by considering absolute values of respective differences between the respiratory pulse variation signals and their average. These absolute values may then correspond to the second data values. Hence, in particular, the fit respiration function may be determined by considering absolute values of respective differences between the respiratory pulse variation signals and their average, thereby folding the portion of the respiratory pulse variation signals below an average value thereof up to the upper portion, and by fitting the second functional prototype to the so obtained values.

In case the fit respiration function is determined by first determining an envelope respiration curve for the previously determined respiratory pulse variation signals and by then determining the fit respiration function based on the envelope respiration curve, in order to avoid any bias from the calculatory steps involved, the envelope respiration curve is preferably calculated analogously to the envelope signal curve, but is associated with the respiratory pulse variation signals instead of the measured pulse signals. More generally, the fit respiration function is preferably calculated based on the data values, i.e. the second data values, to which it is to be fitted, i.e. the envelope respiration curve or the data values derived differently from the respiratory pulse variations signals, for instance, analogously to the fit envelope signal function, with the exception that the data values to which it is to be fitted are different, namely are associated with the respiratory pulse variation signals instead of the measured pulse signals. That is, for example, if the Cauchy-Lorentz function is used as functional prototype to determine the fit envelope signal function, also the Cauchy-Lorentz function is preferably used as functional prototype to determine the fit respiration function. However, how, for instance, before the fitting, the number of data values is reduced for the entire fitting, may be determined based on characteristics of the data values, i.e. for instance, whether they correspond to an envelope curve or a curve derived from an oscillatory signal by considering its absolute values. Hence, how, for instance, before the fitting, the number of data values are reduced may be different for the first data values and the second data values, i.e. the first and the second fitting, respectively. In an embodiment the indicator determination unit is configured to determine the absolute respiratory pulse variation curve by considering absolute values of respective differences between the respiratory pulse variation signals and their average, and to reduce the number of second data values by determining one second data value for each local maximum of the absolute respiratory pulse variation curve.

The indicator that is representative for the fluid responsiveness parameter can be determined based on the fit envelope signal function and the fit respiration function. Preferably, the indicator that is representative for the fluid responsiveness parameter is determined based on at least one parameter of the fit envelope signal function and at least one parameter of the fit respiration function. For example, an indicator that is representative for a patient's volume responsiveness can be determined based on a ratio between a maximum of the fit envelope signal function and a maximum of the fit respiration function. Such a ratio, or a function of this ratio, particularly its inverse, represents an appropriate indicator that is representative for the patient's volume responsiveness.

In an embodiment further data values are determined by determining a further absolute respiratory pulse variation curve for the respiratory pulse variation signals, wherein, in a further fitting, a further functional prototype, which depends on a further fit parameter to be modified during the fitting, is fitted to the further data values such that a further fit respiration function results, wherein the indicator that is representative for the fluid responsiveness parameter is determined based further on the further fit respiration function. Also the further fitting may be performed such that a), before the further fitting, the number of further data values is reduced for the entire further fitting, and/or b) an initial value is determined for the further fit parameter based on characteristics of the further data values which are related to characteristics of the further functional prototype and/or based on a value of the further fit parameter known from a previous further fitting, and/or c) the further fitting is carried out in several stages, wherein the number of further data values used for the further fitting is increased from stage to stage and wherein in a current stage a value of the further fit parameter determined in a previous stage is used as initial value for the further fit parameter in the current stage. The further functional prototype is preferably the same as the second functional prototype. However, the further absolute respiratory pulse variation curve is preferably different from the second absolute respiratory pulse variation curve. It is also possible that several such further fittings are performed, i.e. two, three or more further fittings, wherein the indicator that is representative for the fluid responsiveness parameter can then be determined based further on the several further fit respiration functions.

In a further aspect of the present invention a method for determining an indicator that is representative for a fluid responsiveness parameter is presented, wherein the method comprises:

- providing a sequence of measured pulse signals of a patient over a time period corresponding to a plurality of subsequent respiratory cycles of the patient by a pulse signals providing unit, wherein the sequence of measured pulse signals has been detected by a non-invasive pulse measurement method,
- carrying out a determination procedure adapted to determine an indicator that is representative for a fluid responsiveness parameter based on the provided sequence of pulse signals by an indicator determination unit, wherein the determination procedure includes a determination of data values based on the provided sequence of pulse signals and a fitting of a provided functional prototype, which depends on a fit parameter to be modified during the fitting, to the determined data values, wherein the indicator determination unit is configured such that a), before the fitting, the number of data values is reduced for the entire fitting, and/or b) an initial value is determined for the fit parameter based on characteristics of the data values which are related to characteristics of the functional prototype and/or based on a value of the fit parameter known from a previous fitting, and/or c) the fitting is carried out in several stages, wherein the number of data values used for the fitting is increased from stage to stage and wherein in a current stage a value of a fit parameter determined in a previous stage is used as initial value for the fit parameter in the current stage.

In another aspect of the present invention, a computer program for determining an indicator that is representative for a fluid responsiveness parameter is presented, wherein the computer program comprises program code means for causing an apparatus as defined by any of claims 1 to 12 to carry out the steps of the method as defined in claim 13.

It shall be understood that the apparatus of claim 1, the method of claim 13 and the computer program of claim 14, have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
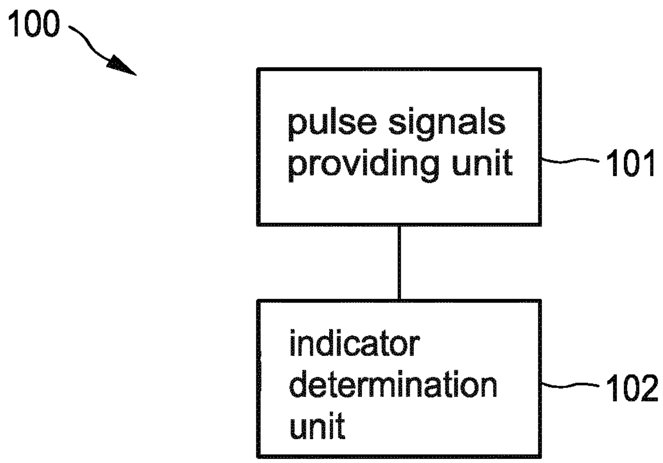
FIG. 1 shows schematically and exemplarily an apparatus for determining an indicator that is representative for a fluid responsiveness parameter.

FIG. 1 shows schematically and exemplarily an apparatus 100 for determining an indicator that is representative for a fluid responsiveness parameter. The apparatus 100 comprises a pulse signals providing unit 101 configured to provide a sequence of measured pulse signals of a patient over a time period corresponding to a plurality of subsequent respiratory cycles of the patient. The sequence of measured pulse signals has been detected by a non-invasive pulse measurement method. The apparatus 100 further comprises an indicator determination unit 102 configured to carry out a determination procedure adapted to determine an indicator that is representative for a fluid responsiveness parameter based on the provided sequence of pulse signals. The determination procedure includes a determination of data values s0, S0, S0', S0" based on the provided sequence of pulse signals and the fitting of a provided functional prototype, which depends on a fit parameter to be modified during the fitting, to the determined data values s0, S0, S0', S0". The indicator determination unit 102 is configured such that a), before the fitting, the number of data values s0, S0, S0', S0" is reduced for the entire fitting, and/or b) an initial value is determined for the fit parameter based on characteristics of the data values s0, S0, S0', S0" which are related to characteristics of the functional prototype and/or based on a value of the fit parameter known from a previous fitting, and/or c) the fitting is carried out in several stages, wherein the number of data values s0, S0, S0', S0" used for the fitting is increased from stage to stage and wherein in a current stage a value of a fit parameter determined in a previous stage is used as initial value for the fit parameter in the current stage. As indicated in FIG. 1, the apparatus 100 may comprise a connection between the pulse signals providing unit 101 and the indicator determination unit 102 via which the pulse signals providing unit 101 can provide the sequence of measured pulse signals to the indicator determination unit 102.

Figure 2:
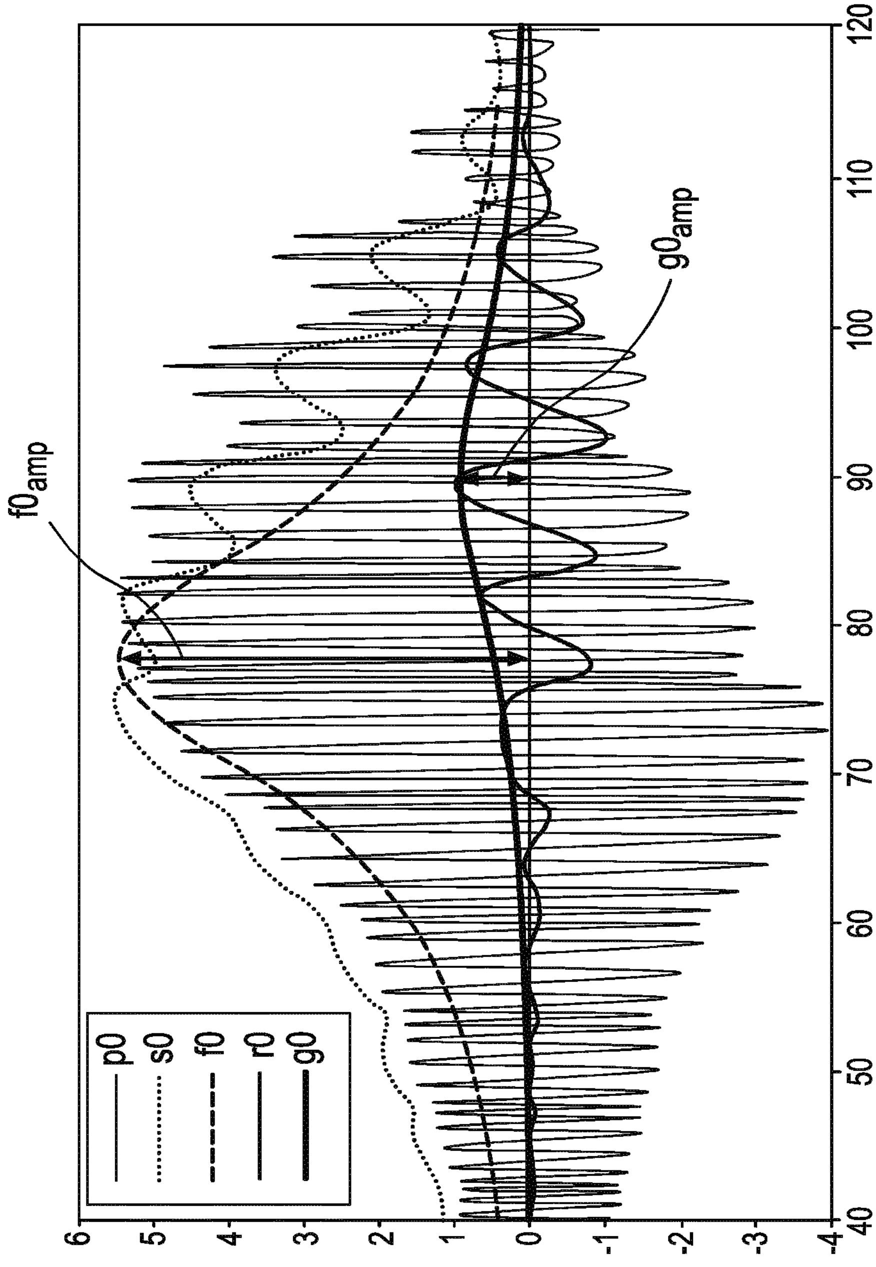
FIG. 2 shows schematically and exemplarily several curves which depend on applied pressure which has been applied by using a pressure cuff.

FIG. 2 illustrates schematically and exemplarily how an indicator that is representative for a patient's volume responsiveness can be determined based on a provided sequence of measured pulse signals that has been detected using a pressure cuff, wherein the pressure applied in the pressure cuff is continuously increased in the course of the measurement period. The horizontal axis of the graph shown in FIG. 2 indicates the pressure applied in the pressure cuff, and could therefore also be viewed as a time axis. The vertical axis indicates a pressure measured by the pressure sensor of the pressure cuff. The measured pulse signals are represented as pulse signals p0 oscillating around an average value thereof. Based on the pulse signals p0, data values s0 are determined by determining an envelope signal curve for the pulse signals p0. The data values s0 may be regarded as being, or being values of, the envelope signal curve. The functional prototype provided for fitting is in this case a bell-shaped Cauchy-Lorentz function of the form $$f(x) = \frac{f_{amp}}{1 + \left(\frac{x - f_{max}}{f_{bw}}\right)^2}, \quad (1)$$

wherein x is the pressure or time indicated on the horizontal axis, the parameter $f_{amp}$ is decisive for the amplitude of the bell-shaped curve of the functional prototype, the parameter $f_{max}$ is decisive for the location of the maximum on the time-axis or pressure-axis and the parameter $f_{bw}$ is decisive for the width at half maximum. Fitting this functional prototype, which is in this case considered as a first functional prototype, to the determined envelope signal curve s0 results in a fit envelope signal function f0, which represents an idealized curve progression of the envelope signal curve s0 over the plurality of respiratory cycles in the measurement period without comprising pulse variations caused by ventilation or respiration induced heart-lung interaction. By taking the difference between the envelope signal curve s0 and the fit envelope signal function f0, respiratory pulse variation signals r0 corresponding to the pulse variations caused by ventilation or respiration induced heart-lung interaction over the plurality of respiratory cycles are determined, wherein, like the pulse signals p0, also the respiratory pulse variation signals r0 are represented as oscillating around an average value thereof. Then, in analogy to how the envelope signal curve s0 was determined from the pulse signals p0, an envelope respiration curve is determined by determining an envelope curve for the previously determined respiratory pulse variation signals r0. A second functional prototype $$g(x) = \frac{g_{amp}}{1 + \left(\frac{x - g_{max}}{g_{bw}}\right)^2}, \quad (2)$$

which is in this case of the same bell-shaped Cauchy-Lorentz type as the first functional prototype, is provided. In particular, x is again the pressure or time indicated on the horizontal axis, the parameter $g_{amp}$ is decisive for the amplitude of the bell-shaped curve of the functional prototype, the parameter $g_{max}$ is decisive for the location of the maximum on the time-axis or pressure-axis and the parameter $g_{bw}$ is decisive for the width at half maximum. By fitting the second functional prototype to the previously determined envelope respiration curve, a fit envelope respiration function g0 is determined, which represents an idealized curve progression of the envelope respiration curve over the plurality of respiratory cycles in the measurement period. Instead of determining an envelope respiration curve for the respiratory pulse variation signals r0 and fitting the second functional prototype to the envelope respiration curve, it may be preferred to fit the second functional prototype to data values derived more directly from the respiratory pulse variation signals r0, i.e., for instance, by considering absolute values of respective differences between the respiratory pulse variation signals and their average, thereby folding up their portion below their average value up to the upper portion. Hence, the fit envelope respiration function g0 might be understood more generally as a fit respiration function g0.

Finally, an indicator VR that is representative for the patient's volume responsiveness is determined as the ratio between the value $g0_{amp}$ of the parameter $g_{amp}$ for the fit respiration function g0 and the value $f0_{amp}$ of the parameter $f_{amp}$ for the fit envelope signal function f0, i.e.

$$VR = \frac{g0_{amp}}{f0_{amp}}. \quad (3)$$

Conventionally, the pulse pressure variation is calculated by $$PPV = \frac{PP_{max} - PP_{min}}{\frac{1}{2}(PP_{max} + PP_{min})}, \quad (4)$$

wherein $PP_{max}$ and $PP_{min}$ are the maximal and minimal pulse pressure, respectively, within one single respiratory cycle. Hence, it estimates a magnitude of pulse variations caused by the patient's respiration. In the procedure described above with reference to FIG. 2, the magnitude of the pulse variations caused by the patient's respiration is represented by the parameter $g0_{amp}$. Similar to the calculation of the pulse pressure variation according to above equation (4) as indicator for the patient's volume responsiveness, the parameter $g0_{amp}$ is "normalized" in equation (3), namely by division through $f0_{amp}$, which indicates a magnitude of the pulse variations caused by heart beats. Therefore, the volume responsiveness indicator obtained according to equation (3) may also be viewed as being indicative for the conventional indicator obtained according to equation (4). Differences might arise from the circumstance that the procedure leading to equation (3) does not rely on single maximum/minimum values of measured pulse pressure variations corresponding to one single heartbeat, but instead takes all pulse signals measured in the measurement time into account.

The determination procedure described above with reference to FIG. 2 is an example of a determination procedure used for determining an indicator that is representative for a fluid responsiveness parameter, i.e. a patient's volume responsiveness, which involves a fitting algorithm and which can therefore be computationally very intensive and hence time consuming. In the procedure described above, this problem can be particularly present, since two fittings are involved. FIGS. 3 to 10 illustrate how this problem can be alleviated using the apparatus 100.

Figure 3:
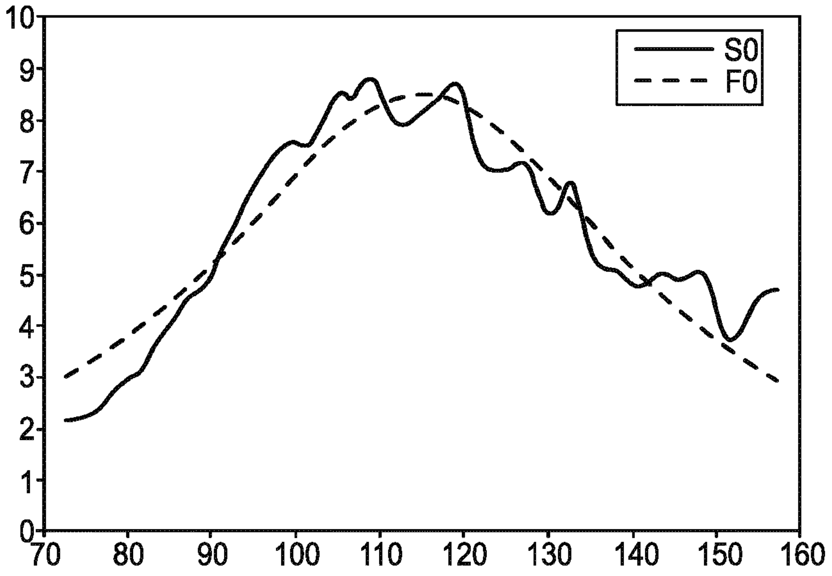
FIGS. 3 to 11 show curves schematically and exemplarily illustrating several determination procedures.

FIG. 3 shows, like FIGS. 4 to 11, schematically and exemplarily a graph whose axes correspond to the axes of the graph shown in FIG. 2. The graph of FIG. 3 includes data values S0 that have been determined based on a provided sequence of pulse signals, and a fit function F0 corresponding to a fitting of the provided functional prototype to the data values S0. In the illustrated embodiment, the data values S0 are not the values, i.e., for instance, sampled values, of the measured pulse signals, but have been determined based on a function derived from the sequence of measured pulse signals, wherein the function might be viewed as corresponding to an envelope signal curve like the envelope signal curve s0 in FIG. 2. The form of the fit function F0 in FIG. 3 corresponds to that of a provided functional prototype, which is, in this case, again a Cauchy-Lorentz function. The fit function F0 has been fitted to the data values S0, wherein the values of the fit parameters have been determined, i.e. modified starting from respective initial values, during the fitting. For fitting the fit function F0 to the data values S0, all of the data values S0 have been taken into account.

Figure 4:
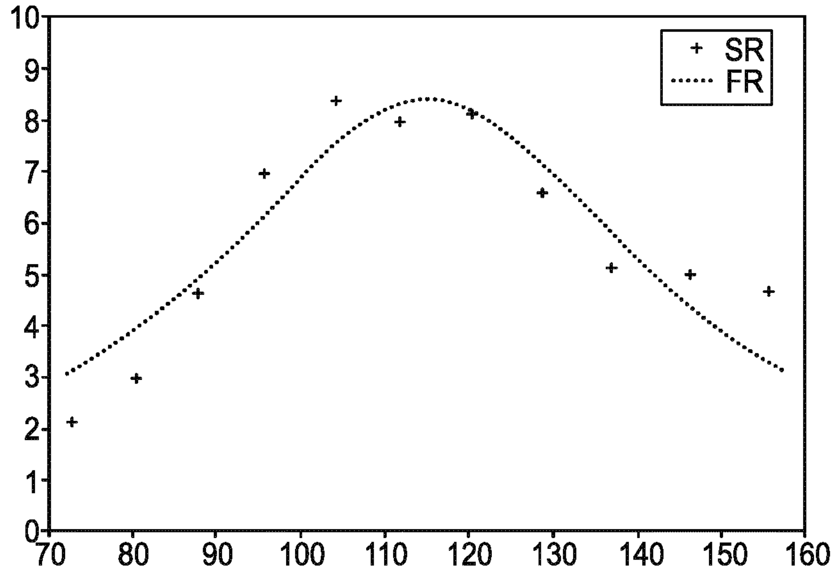

FIG. 4 corresponds to FIG. 3, wherein, however, instead of the full set of data values S0 and the corresponding fit function F0, a reduced number of data values SR and a corresponding fit function FR fitted to the reduced number of data values SR is plotted. The data values SR were obtained by selecting every thousandth of the data values S0. The number of data values S0 used for the fitting has thereby been reduced to 0.1 percent. The fitting was carried out using the same functional prototype as used to arrive at the graph of FIG. 3, namely a Cauchy-Lorentz function.

Figure 5:
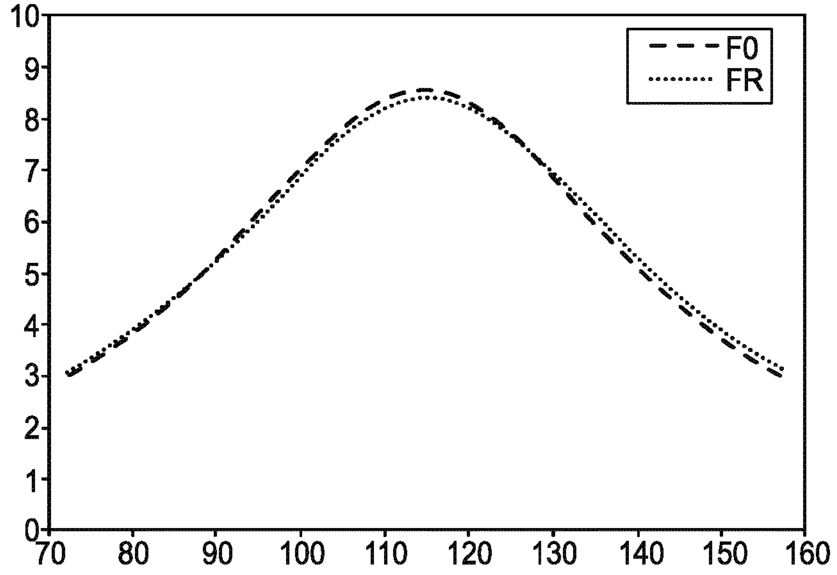

In FIG. 5, which relates to FIGS. 3 and 4, no data values are plotted, but only the fit functions F0 and FR resulting, respectively, from the fitting to the entire set of data values S0 and the reduced set of data values SR. It can be seen from FIG. 5 that even though the number of data values used to arrive at the reduced fit function FR was reduced by 99.9 percent compared to the entire number of data values S0, the reduced fit function FR only deviates by a relatively small amount from the fit function F0. The time required for fitting the functional prototype to the reduced number of data values, however, was substantially reduced compared to the time required for fitting the functional prototype to the entire number of data values S0. Since the indicator that is representative for the fluid responsiveness parameter, i.e. the patient's volume responsiveness, is determined from the final fit parameters resulting from the fitting, such as, like in above equation (3), the maximum of the fit function, the indicator can be determined substantially faster based on the fitting to the reduced number of data values resulting in the fit function FR. Moreover, since the fit function FR deviates only by a relatively small amount from the fit function F0, the faster determination of the indicator does not necessarily negatively affect the accuracy of the determined indicator.

Reducing the number of data values to be considered for fitting is not the only way to allow for a faster fitting and, therefore, a faster determination of the indicator that is representative for the patient's volume responsiveness or fluid responsiveness based on the fitted fit function. In particular, additionally or alternatively, the values of the one or more fit parameters on which the provided functional prototype depends and whose values are to be determined by fitting can be estimated before the fitting, wherein the estimated values may be used as initial values of the fit parameters for the fitting. This is schematically and exemplarily illustrated by FIGS. 6 and 7.

Figure 6:
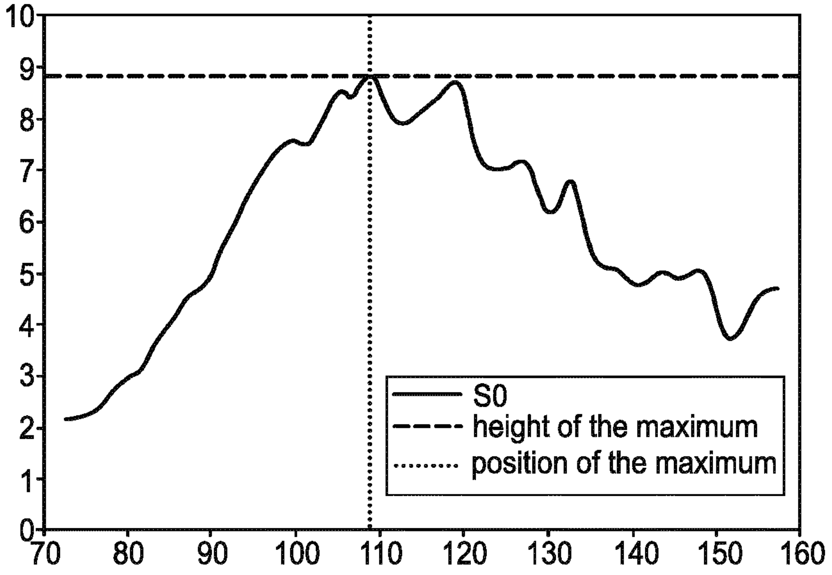
Figure 7:
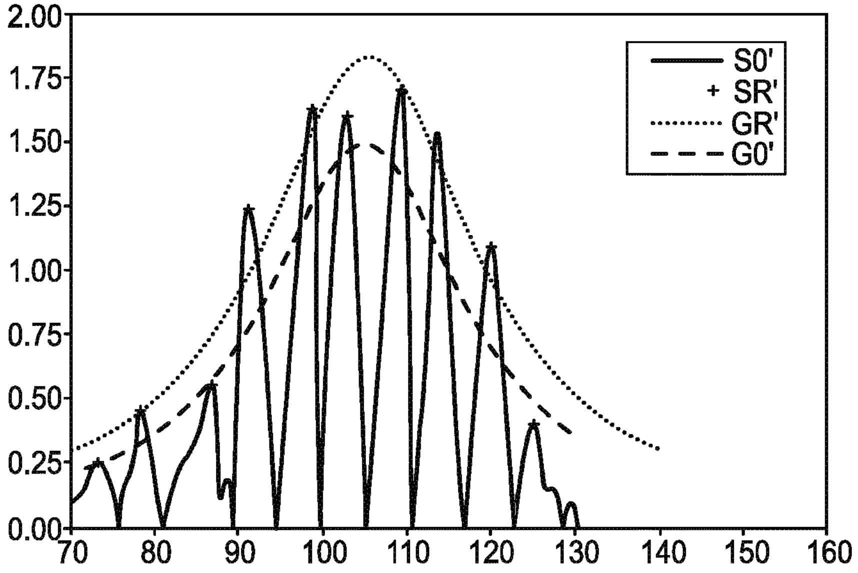

FIGS. 6 and 7 relate to an embodiment in which the functional prototype is, again, a Cauchy-Lorentz function. The Cauchy-Lorentz function has a first fit parameter being indicative of the height of its maximum and a second fit parameter being indicative of the position of its maximum, as already explained in relation to above equations (1) and (2).

FIG. 6 illustrates an embodiment in which the indicator determination unit 102 is configured such that an initial value is determined for the fit parameter based on characteristics of the data values S0 which are related to characteristics of the functional prototype. In the particular embodiment illustrated, the indicator determination unit 102 is configured to determine a height of a maximum of the data values S0 and a position of the maximum of the data values S0, and to determine these values as initial values for the first and the second fit parameter, respectively. The initially assumed fit function, i.e. the fit function assumed at the beginning of the fitting, will in this way be well adapted to the data values S0 such that the amount of fitting to be done can be decreased.

Generally, the amount of fitting needed can also be decreased by only considering those data values for the fitting that capture the characteristics of the entire set of data values that are relevant in respect of the functional prototype. Hence, not only can the initially assumed fit function be adapted to the data values to which it is to be fitted, but also the subset of data values to which the fit function is to be fitted can be adapted to the type of the fit function. This is schematically and exemplarily illustrated in FIG. 7.

FIG. 7 shows a graph in which data values S0' are plotted that have been determined based on the sequence of measured pulse signals using a different kind of preprocessing as compared to the data values S0. The data values S0', which may be referred to as second data values, might be viewed as being derived from signals corresponding to the respiratory pulse variation signals r0 shown in FIG. 2, and hence as being derived from data values corresponding to the data values S0, which may be referred to as first data values. The data values S0' have in this case been derived by considering absolute values of respective differences between signals corresponding to the respiratory pulse variation signals r0 as shown in FIG. 2 and an average value thereof, i.e. by folding up a portion of the corresponding signals below an average value thereof up to the upper portion, and without further determining an envelope curve also for these signals. Hence, the data values S0' correspond to an absolute respiratory pulse variation curve that is not an envelope respiration curve. The data values S0' comprise a series of peaks which vary in amplitude, i.e. height. Since, in this embodiment, the characteristic of interest of the data values S0' is still the progression in amplitude of the peaks, i.e. as opposed to the shape of any single one of the peaks, the number of data values considered for fitting can be reduced to those data values which capture this characteristic of interest, i.e. which capture the progression in peak amplitudes, i.e. heights.

In the illustrated example, the data values considered for fitting have been reduced to the data values corresponding to the local maxima. The resulting reduced set of data values is annotated by SR' in FIG. 7. While a fitting to the entire set of data values S0' results in a fit function G0', a fitting to the reduced set of data values SR' results in a fit function GR'. In this case, the deviation of the fit function GR' from the fit function G0' is noticeable, due to the rather large variations in the original data values S0'. Nevertheless, GR' allows for a good prediction of the fit parameters corresponding to G0'. Particularly the position of the maximum of GR' is close to the position of the maximum of G0', and also the full width at half maximum of GR' is a good estimate of the full width at half maximum of G0'. Still, it may be preferred to apply a predefined scaling factor on the data values S0' before fitting or on the fit function GR'. In this way, it can be taken into account that by considering only the local maxima SR' of S0' for fitting, the height of the fit maximum will always be larger than when fitting to all data values S0'.

A further additional or alternative way to reduce the time needed for fitting and therefore also for determining the indicator that is representative for the fluid responsiveness parameter based on the fit function resulting from the fitting, is schematically and exemplarily illustrated in FIGS. 8 to 11.

FIGS. 8 to 11 relate to an embodiment according to which the fitting is carried out in several stages, wherein the number of data values used for the fitting is increased from stage to stage and wherein in a current stage a value of a fit parameter determined in a previous stage is used as initial value for the fit parameter in the current stage. In particular, in the embodiment illustrated by FIGS. 8 to 11, the indicator determination unit 102 is configured such that the fitting is carried out in three stages, wherein in a first stage a first percentage of the data values, in a following second stage a higher, second percentage of the data values and in a following third stage 100 percent of the data values are used.

Figure 8:
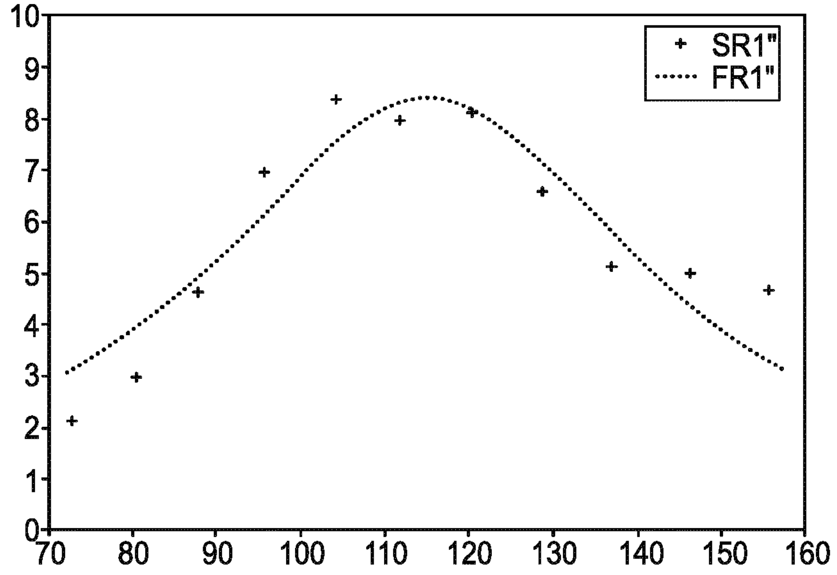

The data values SR1" corresponding to the first percentage of the entire set of data values S0" are plotted in the graph of FIG. 8 together with the fit function FR1" fitted to the data values SR1". In the illustrated embodiment, the original data values S0" correspond to the original data values S0 from the embodiment described with respect to FIGS. 3 to 5. Moreover, the reduced set of data values SR1" corresponds to the reduced set of data values from the embodiment described with respect to FIGS. 3 and 5. That is to say, the first percentage is 0.1 percent in this case.

Figure 9:
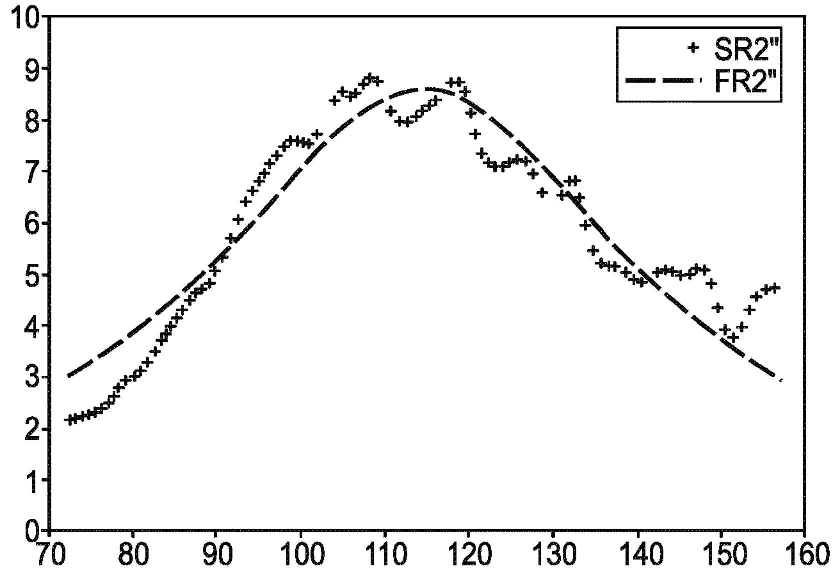

In the graph of FIG. 9, the set of data values SR2" corresponding to the second, higher percentage of the entire set of data values S0" are plotted together with the fit function FR2" fitted to the data values SR2". The second percentage is chosen to be 1 percent in this case.

Figure 10:
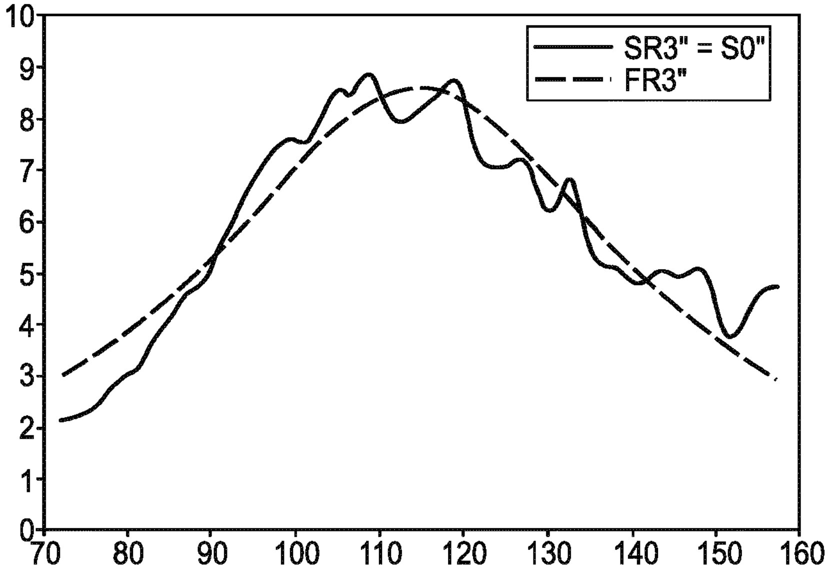

While FIGS. 8 and 9 illustrate the first and, respectively, second stage of the entire fitting process, the third and final stage of the entire fitting process in this embodiment is illustrated in FIG. 10.

In the graph of FIG. 10, data values SR3" corresponding to the entire set of data values S0" are plotted together with a fit function FR3" fitted to the data values SR3"=S0".

In the illustrated embodiment, the part of the fitting process carried out at the second stage comprised a fitting of the provided functional prototype to the data values SR2" that used, as initial values for the one or more fit parameters of the functional prototype, the final values resulting from the first stage, i.e. the fit parameters describing the fit function FR1". Hence, the time needed for fitting at the second stage could be performed in less time as compared to the time that would have been needed if the functional prototype would have been fitted to the data values SR2" based on generic initial values for the fit parameters. Likewise, the fitting executed at the third stage comprise a fitting of the functional prototype to the data values SR3"=S0" that was initiated with values of the one or more fit parameters corresponding to the final values of the fit parameters resulting from the fitting at the second stage, i.e. that was based on the fit function FR2" as initial fit function. Hence, also the fitting at the third stage required less time than what would have been needed for fitting the functional prototype to the data values SR3", which correspond to the entire set of data values S0", based on generic initial values for the fit parameters.

Figure 11:
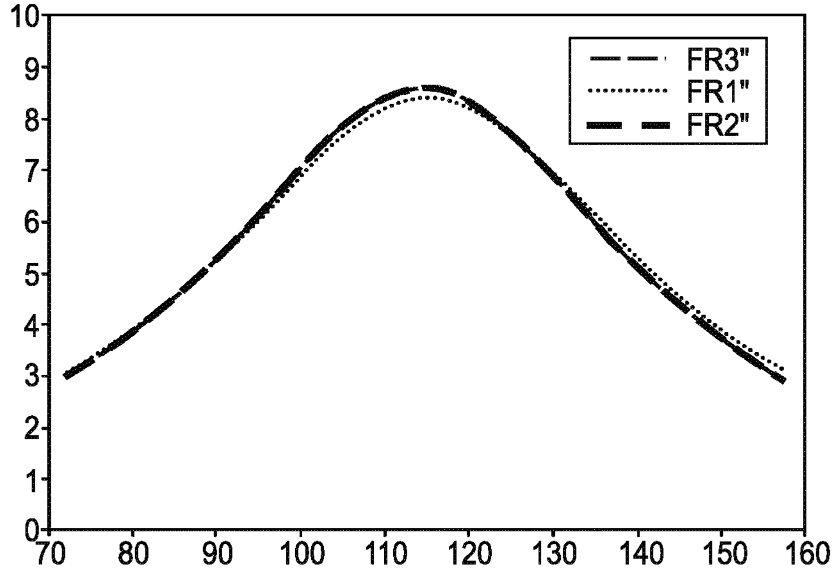

In the graph of FIG. 11, the final fit functions FR1", FR2", FR3" resulting, respectively, from the three stages of fitting are plotted for comparison. While the fit function FR1" still deviates from the fit function FR3", even though by only a relatively small amount, the deviation of the fit function FR2" from the fit function FR3" is hardly noticeable. Hence, already the fit function FR2" resulting from the second stage may be viewed as an accurate fit of the entire set of data values S0".

For this reason, in some embodiments, the indicator determination unit 102 may be configured such that the fitting is carried out in several stages, wherein, after the fitting has been carried out in a stage, it is determined whether the fitted fit parameter is in conformance with an abort criterion, wherein, if this is the case, the fitting is terminated. For instance, in the embodiment illustrated by FIGS. 8 to 11, one or more of the fit parameters may already be in conformance with the abort criterion after the fitting at the second stage has been carried out, such that the entire fitting is terminated. In some embodiments, the fitting may only be terminated if more than one or all of the fit parameters are in conformance with respective abort criteria.

While abort criteria may be used to terminate fitting if the current fit function is already accurate enough, abort criteria may also be used to terminate fitting if it is concluded, for instance, after one of the stages of a multiple staged fitting process, that the fit results will likely not lead to any valid fit function at all.

For instance, when fitting to a bell-shaped Cauchy-Lorentz function, the fit parameter corresponding to the position of the maximum of the function may be expected to lie in a certain range for a given set of data values. The range may be defined by one or both of an upper limit and a lower limit, wherein the lower limit may correspond to the position of the first data value and the upper limit may correspond to a multiple of a signal length, the multiple being, for instance, any value from 1 to 5.

If, then, for instance, the fitting is carried out in three stages, wherein at the first stage $1/250$ of the of the data values are used, at the second stage $\sqrt{1/250}$ of the data values are used and at the third stage all data values are to be used, the final stage does not need to be calculated if the position of the maximum of the fitted function resulting from the second stage is not within the previously defined range, because it can be expected that the final result, particularly the final position of the maximum resulting from the final stage, will not be a valid result.

Figure 12:
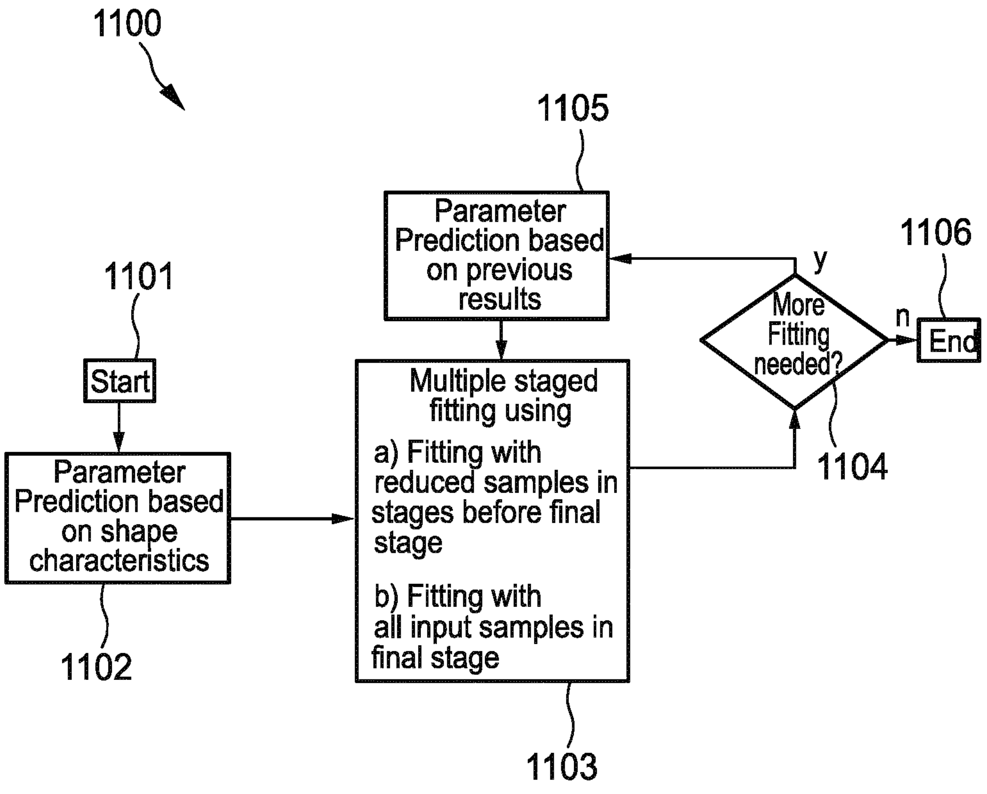
FIG. 12 illustrates schematically and exemplarily steps of a determination procedure for determining an indicator that is representative for a fluid responsiveness parameter.

FIG. 12 schematically and exemplarily illustrates a determination procedure 1100 according to a combination of previously described embodiments.

In a first step 1101, data values s0, S0, S0', S0" are determined based on a sequence of measured pulse signals that has been provided.

In a second step 1102, initial values are determined for each of the one or more fit parameters of the functional prototype that is to be fitted to the data values s0, S0, S0', S0". The initial values are determined based on characteristics of the data values s0, S0, S0', S0" that correspond to characteristics of the functional prototype for which the respective fit parameters are indicative. For instance, if the functional prototype is a bell-shaped function with a first parameter being indicative of the height of the maximum of the bell-shaped function and a second fit parameter being indicative of the position of the maximum of the bell-shaped function, in step 1102 a height of a maximum of the data values s0, S0, S0', S0" and a position of the maximum of the data values s0, S0, S0', S0" can be determined as initial values for the first and the second fit parameter.

In a following step 1103, multiple staged fitting is carried out using the initial values determined in step 1102 as initial values for the fit parameters in the first stage. The multiple staged fitting carried out in step 1103 can, for instance, be carried out as described with reference to FIGS. 7 to 10.

In a subsequent step 1104, it is decided whether a further set of data values needs to be considered for a further fitting, wherein the further set of data values would be determined based on a further sequence of measured pulse signals. This decision may be made separately for the set of first data values determined for a first fitting and the set of second data values determined for a second fitting performed for a same sequence of measured pulse signals. The decision whether more fitting is needed may be made in accordance with an abort criterion similar to the one possibly employed for determining, after any of the non-final stages of the multiple staged fitting, whether the multiple staged fitting is to be terminated.

If it is decided in step 1104 that further fitting is needed, initial fit parameters for the further fitting are estimated in step 1105 based on the final fit parameters resulting from the previous fitting performed in step 1103. Multiple staged fitting as performed in step 1103 is then repeated for the further set of data values, with the exception that, as initial values for the fit parameters in the first stage of the multiple staged fitting carried out in the repeated step 1105, no values describing characteristics of the further data values corresponding to characteristics of the functional prototype for which the fit parameters are indicative are used, but, instead, the final values of the fit parameters resulting from the multiple staged fitting to the previous set of data values are used. Hence, in an embodiment illustrated by FIG. 12, the indicator determination unit 102 determines an initial value for a fit parameter based on a value of the fit parameter known from a previous fitting.

The cycle defined by steps 1103, 1104 and 1105 is repeated as long as it is decided in step 1104 or its repetitions that more fitting is needed, i.e., for instance, as long as an abort criterion is not met, and as long as not all provided sets of data values have been used for fitting. For instance, if four sequences of measured pulse signals have been provided by the pulse signals providing unit, or a single sequence of measured pulse signals corresponding to four inflations of the pressure cuff, and if, based on the provided sequences or, respectively, sequence, four sets of data values have been determined, each of which corresponds to one sequence or, respectively, inflation, then the cycle defined by steps 1103, 1104 and 1105 will be carried out a maximum number of four times.

Whenever it is decided that no more fitting is needed, i.e., in step 1104 or its repetitions, a step 1106 follows. In step 1106, the indicator that is representative for the fluid responsiveness parameter is determined based on the final fit function resulting from the previous, i.e. last, fitting.

If, for instance, the apparatus 100 configured as described above with reference to FIG. 12 is used on a set of 540 representative records for calculating a PPV, an SVV or an SPV, wherein for each record 11 individual fits are calculated for 2 different kinds of input samples and wherein a bell-shaped Cauchy-Lorentz function is used as functional prototype, the following performance optimization can be observed.

In the non-optimized case, i.e. if all data values are used for the fitting and the fitting is carried out in a single stage, the time required for the fitting of all records amounts to 64 seconds in total, the average time required for the fitting per record being 0.119 seconds. For each record, an average of 49 fitting iterations on all of the approximately 13000 input samples can be observed.

In the optimized case, for each of the two kinds of input samples the final fit parameters of a previous fit were used as initial fit parameters of the fit to be done. In this case, the time required for the fitting of all records amounts to 24 seconds, the average time required for the fitting per record being 0.044 s, which is approximately 38 percent of the time required in the non-optimized case. For each record, an average of 38 fitting iterations on approximately 50 reduced input samples, an average of 23 fitting iterations on approximately 800 reduced input samples and an average of 11 fitting iterations on all approximately 13000 input samples can be observed.

Figure 13:
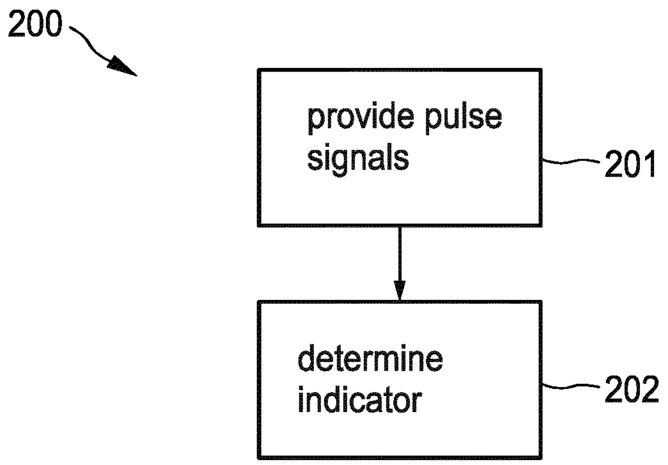
FIG. 13 shows a flow chart exemplarily illustrating a method for determining an indicator that is representative for a fluid responsiveness parameter.

FIG. 13 illustrates schematically and exemplarily an embodiment of a method 200 for determining an indicator that is representative of a fluid responsiveness parameter. The method comprises, in a first part 201, providing a sequence of measured pulse signals of a patient over a time period corresponding to a plurality of subsequent respiratory cycles of the patient by a pulse signals providing unit 101, wherein the sequence of measured pulse signals has been detected by a non-invasive pulse measurement method. The measurement might be performed using a pressure cuff, wherein the pressure applied in the pressure cuff is continuously increased or decreased in the course of a measurement period. In a second part 202, the method 200 comprises carrying out a determination procedure adapted to determine an indicator that is representative for the fluid responsiveness parameter based on the provided sequence of pulse signals by an indicator determination unit 102, wherein the determination procedure includes a determination of data values s0, S0, S0', S0" based on the provided sequence of pulse signals and a fitting of a provided functional prototype, which depends on a fit parameter to be modified during the fitting, to the determined data values s0, S0, S0', S0". The indicator determination unit 102 is configured such that a), before the fitting, the number of data values s0, S0, S0', S0" is reduced for the entire fitting, and/or b) an initial value is determined for the fit parameter based on characteristics of the data values s0, S0, S0', S0" which are related to characteristics of the functional prototype and/or based on a value of the fit parameter known from a previous fitting, and/or c) the fitting is carried out in several stages, wherein the number of data values used for fitting is increased from stage to stage and wherein in a current stage a value of a fit parameter determined in a previous stage is used as initial value for the fit parameter in the current stage. The determination procedure carried out in the second part 202 of the method 200 can be a determination procedure of the kind described above, for example, with reference to FIG. 12.

Although in the above described embodiments the functional prototype was a bell-shaped function, other functional prototypes may be used. The runtime of a fitting algorithm can be reduced compared to simply applying the fitting algorithm to the entire set of data values by reducing, for instance, the total number of iterations in the fitting algorithm or the number of data values actually used for fitting.

If the number of data values actually used for fitting is reduced, the reduction is preferably done in a way that keeps the main characteristics of the data values in relation to the functional prototype.

The total number of iterations needed, and therefore the total time required for fitting, can be reduced, for instance, by initially predicting parameters of the functional prototype that are preferably close to the final parameters to be determined by the fitting. When successive fitting of several sets of data values with similar characteristics is done, the final fit parameters of a previous fit can be used as initial fit parameters of the fit to be done. While in the context of determining an indicator that is representative of a patient's volume responsiveness, the sets of data values may correspond to subsequent breathing or ventilation cycles of the patient, in the more general context of reducing the runtime of fitting algorithms, the different sets of data values may comprise similar characteristics due to other reasons than the cyclic nature of breathing or ventilation.

The runtime of a general fitting algorithm can also be reduced by iteratively, i.e. in stages, applying the fitting algorithm, starting with the reduced number of data values and increasing the number of data values in each subsequent stage, wherein, preferably, in the last stage the original, entire number of data values is used for fitting. In such multiple staged fitting, the preferred number of stages may be found depending on the intended application by, for instance, finding the minimum of the total runtime experimentally. In this way, the optimal combination of the number of data values used for the fitting in each stage and the number of stages can be found.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the providing of the sequence of measured pulse signals, the determining of the data values based on the provided sequence of pulse signals, the fitting of the provided functional prototype to the determined data values, a reducing and/or increasing of the number of data values, the determining of an initial values of a fit parameter, any other procedure involved in carrying out the determination procedure, particularly determining the indicator based on the provided sequence of pulse signals, et cetera, performed by one or several units or devices can be performed by any other number of units or devices. These procedures can be implemented as program code means of a computer program and/or as dedicated hardware, particularly as an embedded system.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an apparatus for determining an indicator that is representative of a fluid responsiveness parameter like a fluid responsiveness parameter. The indicator is determined based on a fitting of a functional prototype to data values determined from pulse signals measured over subsequent respiratory cycles. The fitting process is accelerated by a) reducing the number of data values before fitting, b) determining an initial fit parameter value for the functional prototype based on characteristics of the data values and/or a fit parameter value known from a previous fitting, and/or c) carrying out the fitting in several stages, wherein the number of data values used is increased from stage to stage and a fit parameter value determined in a previous stage is used as initial fit parameter value in a current stage. This allows for a faster determination of the fluid responsiveness parameter.

The invention claimed is:

1. An apparatus for determining an indicator representative of a fluid responsiveness during a blood pressure test, the apparatus comprising:

a non-invasive pulse measurement device comprising a pressure cuff and a pressure sensor configured to detect a blood pressure from a patient and generate corresponding pulse signals over a time period corresponding to multiple respiratory cycles, and a processor operatively coupled to a memory storing instructions which, when executed by the processor, cause the processor to:

(i) generate first data values corresponding to an envelope signal curve, the envelope signal curve representing amplitude variations of the pulse signals over time;

(ii) generate second data values corresponding to respiratory pulse variation signals, the respiratory pulse variation signals determined as differences between the envelope signal curve and a first fitted envelope function;

(iii) perform a fitting operation including:

down-sampling first data values and/or second data values in accordance with a Shannon-Nyquist criterion;

determining initial fit parameter values for a functional prototype based on characteristics of the down-sampled first data values and/or second data values;

fitting the functional prototype, having the initial fit parameters, to the first data values to generate the first fitted envelope function;

fitting the functional prototype to the second data values to generate a respiration-based fitted function; and (iv) determine the fluid responsiveness indicator based on at least one parameter of the first fitted envelope function and at least one parameter of the respiration-based fitted function.

2. The apparatus of claim 1, wherein the processor is further configured to reduce the number of first and/or second data values by down-sampling such that a reduced sampling rate satisfies the Shannon-Nyquist criterion with reference to a bandwidth of at least one of:

(i) the functional prototype, (ii) the envelope signal curve, and (iii) the respiratory pulse variation signals.

3. The apparatus of claim 1, wherein reducing the number of data values comprises selecting one data value per predetermined time interval corresponding to a frequency below the maximum frequency contained in the envelope signal curve.

4. The apparatus of claim 1, wherein the processor applies a low-pass filter to the envelope signal curve or the respiratory pulse variation signals prior to reducing the number of data values.

5. The apparatus as defined by claim 1, wherein the functional prototype is a bell-shaped function.

6. The apparatus of claim 5, wherein the functional prototype comprises a bell-shaped Cauchy-Lorentz function having parameters corresponding to amplitude and peak position, and wherein the processor determines a height and position of a maximum of the envelope signal curve as initial values for the fit parameters.

7. The apparatus of claim 1, wherein the fitting operation is executed in three stages in which a first stage uses a first subset comprising a 0.1% of the data values, a second stage uses a 1% of the data values, and a third stage uses 100% of the data values.

8. The apparatus of claim 7, wherein the processor terminates the multi-stage fitting operation early when a fitted parameter obtained in a current stage satisfies an abort criterion.

9. The apparatus of claim 8, wherein the abort criterion comprises determining that a deviation between a fitted parameter obtained in a stage and an expected value of the parameter is below a predetermined threshold.

10. The apparatus of claim 1, wherein the processor represents the measured pulse signals as oscillations around an average value and is further configured to: determine the envelope signal curve; fit the functional prototype to obtain the first fitted envelope function; compute the respiratory pulse variation signals; determine second data values from absolute values of such signals; and fit the functional prototype to obtain the respiration-based function.

11. The apparatus of claim 10, wherein determining the second data values comprises identifying local maxima of absolute respiratory pulse variation signals.

12. The apparatus of claim 1, wherein the pressure cuff includes a fluid-filled pressure sensor airlessly coupled to the patient's tissue.

13. A method for determining an indicator representative of a fluid responsiveness during a blood pressure test, the method implemented by a processor and a non-invasive pulse measurement device, the non-invasive pulse measurement device comprising a pressure cuff and a pressure sensor configured to detect a blood pressure from a patient and generate corresponding pulse signals over a time period corresponding to multiple respiratory cycles, the method comprising:

(i) generating first data values corresponding to an envelope signal curve, the envelope signal curve representing amplitude variations of the pulse signals over time;

(ii) generating second data values corresponding to respiratory pulse variation signals, the respiratory pulse variation signals determined as differences between the envelope signal curve and a first fitted envelope function;

(iii) performing a fitting operation including:

Down-sampling first data values and/or second data values in accordance with a Shannon-Nyquist criterion;

determining initial fit parameter values for a functional prototype based on characteristics of the down-sampled first data values and/or second data values;

fitting the functional prototype, having the initial fit parameters, to the first data values to generate the first fitted envelope function;

fitting the functional prototype to the second data values to generate a respiration-based fitted function; and (iv) determining the fluid responsiveness indicator based on at least one parameter of the first fitted envelope function and at least one parameter of the respiration-based fitted function.

14. A non-transitory computer-readable medium storing instructions that, when executed by a processor of an apparatus comprising a pressure cuff and pressure sensor, cause the processor to perform the method of claim 13.

* * * * *